US006562874B1

(12) United States Patent
Ilardi et al.

(10) Patent No.: US 6,562,874 B1
(45) Date of Patent: May 13, 2003

(54) COMPOSITIONS COMPRISING COMBINATION OF DEFI AND MODIFIED DEFI AND METHODS OF MAKING

(75) Inventors: Leonora Ilardi, Englewood, NJ (US); Lee Ann Gallagher, Morristown, NJ (US); Michael Massaro, Congers, NY (US)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/455,607

(22) Filed: Dec. 7, 1999

(51) Int. Cl.$^7$ ................... B01F 17/06; B01F 17/24; C11D 1/12
(52) U.S. Cl. .................. 516/14; 516/63; 516/909; 516/912; 516/62; 554/49; 554/69; 554/90; 554/92; 510/156; 510/494; 510/495
(58) Field of Search .................. 516/63, 59, 62, 516/14, 909, 912; 554/90, 92, 49, 69; 510/156, 495, 494

(56) References Cited

U.S. PATENT DOCUMENTS

| | | | | |
|---|---|---|---|---|
| 1,881,172 A | * | 10/1932 | Daimler et al. ............... 516/63 |
| 4,476,055 A | | 10/1984 | DuVernet .................... 510/495 |
| 4,515,721 A | * | 5/1985 | Login et al. .................. 554/92 |
| 5,296,627 A | | 3/1994 | Tang et al. ................... 558/34 |
| 5,300,665 A | * | 4/1994 | Tracy et al. .................. 554/92 |
| 5,300,666 A | | 4/1994 | Imperante et al. .......... 556/428 |
| 5,384,421 A | * | 1/1995 | Day et al. ..................... 554/92 |
| 5,646,320 A | | 7/1997 | Cassady et al. ............. 554/149 |
| 5,756,439 A | * | 5/1998 | He et al. ..................... 510/159 |

FOREIGN PATENT DOCUMENTS

| | | |
|---|---|---|
| DE | 43 15 810 | 11/1984 |
| DE | 43 37 035 | 5/1995 |
| EP | 0262420 | 4/1988 |

OTHER PUBLICATIONS

A Novel: Dianionic Surfactant from the Reaction of $C_{14}$—Alkenylsuccinic Anhydride with Sodium Isethionate, Schmidt et al., JAOCS, vol. 71, No. 7 (Jul. 1994).
Surface Active Agents From Isopropenyl Esters: Acylation of isethionic Acid and N—Methyltaurine, Bistline, Jr. et al., Journal of The American Oil Chemists Society vol. 48 (Nov., 1971).

* cited by examiner

Primary Examiner—Daniel S. Metzmaier
(74) Attorney, Agent, or Firm—Ronald A. Koatz

(57) ABSTRACT

Composition may be prepared in a single DEFI reactor comprising mixtures of (1) DEFI (directly esterified fatty acyl isethionate) and (2) a compound produced by the reaction of (a) isethionate with a fatty acid replacement (e.g., a multicarboxylic fatty acid, a fatty acid); or (b) fatty acid with an isethionate replacement (e.g., $C_2$–$C_{24}$ alcohols, $C_2$–$C_{20}$ organic acids, amines). Such mixtures are milder than DEFI alone while retaining substantially same foaming benefit.

6 Claims, No Drawings

COMPOSITIONS COMPRISING COMBINATION OF DEFI AND MODIFIED DEFI AND METHODS OF MAKING

The present invention relates to anionic starting materials/surfactants, particularly those which are prepared from the direct esterification of fatty acids and isethionate (i.e., directly esterified fatty acyl isethionate or "DEFI") and which may be used in personal wash compositions such as, for example, personal wash bars or personal wash shower gel compositions. Specifically, the invention relates to compositions comprising mixtures of DEFI and modified DEFI compounds. The modified DEFI compounds are compounds made in the same DEFI reactor where DEFI is made (from reaction of fatty acid and isethionate) except that the fatty acid is substituted and reacted with isethionate and/or the isethionate is substituted and reacted with fatty acid. As noted, the mixtures may also comprise compounds where the fatty acid substitute and isethionate substitute may react with each other.

BACKGROUND

In personal wash compositions (e.g., bars or liquids), one very common anionic surfactant which is used is acyl isethionate. This compound is milder than soap, yet retains characteristics which consumers associate with good cleaning (e.g., foaming). It would be greatly beneficial to find compounds which are still milder and/or less drying than fatty acid isethionates, while maintaining good foaming profiles. Further, when used in bar preparation, such compounds should be suitable for bar processing conditions.

The acyl isethionate surfactant is commonly produced by the direct esterification of a fatty acid (e.g., $C_{10}$ to $C_{16}$ fatty acid such as lauric fatty acid) and isethionate (e.g., $OHCH_2CH_2SO_3^-Na^+$) in a process commonly known as the "DEFI" process (process for making directly esterified fatty acid isethionate). The DEFI process is conducted in a single DEFI reactor.

Applicants have now discovered that, if either the fatty acid starting component is partially replaced (e.g., with silicone based carboxylic acids, fatty acids derived from Neem oil or castor oil of varying chain distribution, dicarboxylic acids, etc.); and/or the isethionate starting component is partially replaced (e.g., with glycerol, sorbitol, pentaerythritol, amines etc.), not only will the DEFI reactor form the expected directly esterified fatty acid isethionate (from the fatty acid and isethionate which are not partially replaced), but a portion of the final reaction component will also represent combinations of, for example, isethionates modified by the different types of fatty acids (when the standard fatty acid is partially replaced), or alcohol esters or amides (when the isethionate is partially replaced). The cosurfactants produced during the production of the main active (e.g., sodium lauroyl or sodium cocoyl isethionate) are mild and result in milder surfactant mixtures.

That is, the same DEFI reactor will produce mixtures of "standard" fatty acid isethionate and these "modified" DEFI compounds. Applicants are aware of no prior art which teaches or suggests that mixtures of standard and modified DEFI can be produced in the same reactor, let alone that at least some of these mixtures may provide enhanced mildness without sacrificing foaming. It should be noted that a small part of the mixture may also comprise compounds formed by fatty acid replacement reacting with isethionate replacement.

U.S. Pat. No. 5,300,666 to Imperante et al., teaches a process for condensing silicone carboxylates with sodium isethionate under conditions similar to the "DEFI" process (the reaction time of the reference is 5–15 hours versus 90 minutes for standard DEFI reaction; same temperatures of 220–240) to produce high foaming, mild surfactants. This reaction, however produces only a single "modified" DEFI compound. It does not produce mixtures of "standard" and modified DEFI in a single reactor. Further, it teaches only the replacement of standard (e.g., lauric) fatty acid with a silicone based carboxylic acid and fails to teach or suggest the many other possible fatty acid replacements of the subject invention. It also fails to teach that the isethionate portion may be replaced instead of or, in addition to the fatty acid portion. Finally, the process involves longer reaction times than those of the subject invention, 5 to 15 hours versus 90 minutes.

Other references also teach compounds which could be the "modified" DEFI component of the subject invention. U.S. Pat. No. 4,476,055 to Du Vernet, for example, teaches $C_{21}$ dicarboxylic acid isethionates as anionic surfactants; Schmidt et al., in "A Novel Dianionic Surfactant from the Reaction of $C_{14}$-Alkenylsuccinic Anhydric with Sodium Isethionate", JAOCS, 71 (7):695–703 (1994) teach an isethionate reacted with $C_{14}$alkenyl succinic acid; and Bistline et al., in "Surface Active Agents from Isopropenyl Esters: Acylation of Isethionic Acid and N-Methyltaurine", JAOCS 48 (11): 657–60 (1971) teach another isethionate based surfactant made using DEFI-like conditions (e.g. high temperature and acidic catalysts).

Other references teach isethionate-based surfactants made under high temperature and basic catalysts (see, e.g., DE 4,337,035 to Henkel (1995); DE 4,315,810 to Henkel (1994); DE 1,234,708 to General Aniline and Corp. (1967); U.S. Pat. No. 5,296,627 to Tang et al. (assigned to PPG Industries) or JP 04,360,863 to Tosoh Corp. (1992)).

Again, none of these references teach or suggest mixtures of standard DEFI with the modified DEFI produced in the same reactor by at least partially replacing the standard fatty acid and/or isethionate. Further, none of these references teach or suggest that such mixtures may be milder than DEFI alone while maintaining a strong foaming profile.

BRIEF DESCRIPTION OF THE INVENTION

Suddenly and unexpectedly, applicants have discovered new compositions wherein said compositions comprise mixtures of "standard" DEFI (made from reaction of isethionate with C8 to C22 straight chain substantially saturated (preferably greater than 85% saturated) monocarboxylic fatty acids (it should be noted that in mixtures such as "coco" fatty acid, there may be some small percentage of unsaturated fatty acid such as, for example, oleic fatty acid) and DEFIs which have been modified by partially replacing (1–80%, preferably 10–50%, most preferably 10–35%) the fatty acid and/or the isethionate in the reactor so that the replacing material reacts with the fatty acid or isethionate to produce the modified DEFI.

More specifically, the compositions comprise mixtures of:

(a) "standard" DEFI (Isethionate reacted with $C_8$–$C_{22}$, preferably $C_{10}$–$C_{16}$ straight chain substantially saturated non-carboxylic acid); and (b) a DEFI produced by either reacting $C_8$–$C_{22}$ fatty acid with a replacement polyol (e.g., glycerol, sorbitol, pentaerythritol or almost any compound with available OH group), organic acid, or amine or mixtures thereof; or reacting isethionate with a replacement fatty acid (e.g., silicone based carboxylic acid, multicarboxylic fatty acid derived from Neem oil or castor oil of varying chain distribution, dicarboxylic acids).

In a second embodiment of the invention, the invention comprises a process for making a mixture of "standard" DEFI and "modified" DEFI in a single reactor which process comprises: mixing:

(i) about 20 to 50% by wt., preferably 25% to 40% by wt., alkali metal isethionate;

(ii) about 35% to 75% by wt., preferably 45% to 65% by wt. $C_8$–$C_{22}$ straight chain fatty acid;

(iii) about 0 to 20% by wt., preferably 0.1 to 18% by wt. replacement for alkali metal isethionate; and (iv) about 0% to 10% by wt., preferably 0.1 to 9% by wt. replacement for $C_8$–$C_{22}$ straight chain fatty acid;

at a temperature of 180 to 240° C.

wherein an acid catalyst is used; (e.g., zinc oxide, zinc isethionate, or any Lewis acid);

wherein (i) and (ii) and at least one of (iii) or (iv) must be mixed in the reactor.

It should be noted that "replacement" reactants may be combined at the beginning of the reaction or that they may be used at some point after compounds (i) and (ii) have been reacting for awhile (e.g., 5 minutes to 60 minutes).

DETAILED DESCRIPTION OF THE INVENTION

The present invention relates to compositions comprising mixtures of (1) "standard" directly esterified fatty acid ("DEFI") and (2) either (a) product formed from reaction of isethionate and a "replacement" for fatty acid normally used during production of alkali metal ester of $C_8$–$C_{22}$ substantially saturated, straight chain monocarboxylic acid fatty or (b) product formed from the reaction of the substantially saturated, straight chain monocarboxylic acid and a "replacement" for isethionate (e.g., alcohols, organic acids, amines etc.).

Specifically, mixtures of standard "DEFI" (1) and the cosurfactants produced by 2(a) or 2(b) above have been found to enhance mildness (as measured by decreased zein solubilization) while maintaining adequate foaming. Further, the mixtures are produced in a single reactor.

More specifically, a standard "DEFI" reaction is defined as the mixture of a $C_8$–$C_{22}$, generally $C_{10}$ to $C_{16}$ fatty acid (e.g., lauric acid or coco fatty acid) with alkali metal isethionate as follows:

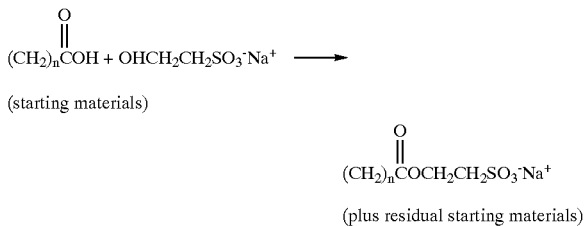

(starting materials)

(plus residual starting materials)

Normally, reaction is conducted at ratio of about 1 to 1 to 2 to 1 fatty acid to isethionate using 0.001–0.05, preferably 0.01 to 0.04 of total reactants by weight of a catalyst (e.g., zinc oxide, zinc isethionate or any Lewis acid including sulfuric acid, p-toluene sulfonic acid, sodium bisulfite etc.) at a temperature of about 150° C. to 250° C., preferably about 200° C. to 250° C. for about 1 to 3 hours.

Both in the "typical" DEFI process and in that of the invention, it is possible to use a little bit of the final product (after made or obtained once) and use this as an emulsifying agent for the reaction. This helps speed up the reaction.

The components of the reaction may be added in any order and, although yields may be better reacting one agent before another, any order of addition is contemplated.

The directly esterified fatty acyl isethionate ("DEFI") formed from this reaction has reasonable mildness properties (as measured by zein solubilization) and good foaming ability (e.g., about 95–100 mls foam in a 100 milliliter graduated cylinder when using about 5% solution).

Typically, the subject invention involves the "replacement" of a portion of one of the two reactants (e.g., sodium isethionate) with, for example in the case of isethionate replacement or modification, alcohol, organic acid or mixtures thereof. Thus, typically, for example, one quarter by weight of the isethionate may be replaced by a 2:1 ratio of glycerol and lactic acid mixture (in reaction with lauric acid, for example) resulting in a final mixture comprising sodium lauroyl isethionate ester, left over lauric acid, left over sodium isethionate in addition to some glycerol monolaurate (from reaction of lauric acid and glycerol) and glycerol monolaurate monolactate.

It is these typical mixtures which have then been analyzed to determine mildness (typically more mild as measured by zein compared to if no isethionate had been replaced) and foaming (typically slightly less foaming, but still adequate).

Replacement/Modification for Isethionate

Typical replacements for the isethionate reactant under standard reaction conditions (e.g., using same catalysts as for DEFI reaction, same perspective ranges, i.e., 150 to 250° C., preferably 200 to 250° C. and same reaction times, i.e., 1 to 3 hours) are polyols, organic acids, amines and mixtures thereof).

Examples of alcohols include any straight or branched chain, cyclic or acyclic molecule containing two or more hydroxy groups (where the position of the hydroxy groups is not critical) such as glycerol, ethylene glycol (example of a 1,2 diol), propylene glycol (example of a 1, 3 diol), meso-erythritol, pentaerythritol, and the like, reduced sugars, such as sorbitol, mannitol, and the like or sugars, preferably pentoses and hexoses, mono or disaccharides, such as glucose, galactose, xylose, lactose, maltose or mixtures thereof.

Examples of organic acid replacement for Isethionate include linear, branched or cyclic compounds containing a hydroxy group alpha or beta to a free carboxylic acid moiety. These include alpha or beta hydroxy acids such as glycolic acid, lactic acid citric acid, salicylic acid, and the like and mixtures thereof.

Examples of amines which may be used to partially replace isethionate include any linear, branched or cyclic compound containing at least one NH2 or NH group. Such compounds include taurine, N-methyl taurine, tris-hydroxyaminomethane, tris-hydroxyaminoethane; amino acids such as glysine, lysine, and the like, hydroxyamines and polyhydroxyamines, such as N, N diethanolamine, N-methyl glucamine, sorbitol amine, and the like; and mixtures thereof.

Typically, anywhere from 5% to 75%, preferably 5% to 50%, more preferably 5% to 20% of the isethionate, on a weight basis, will be replaced so that both isethionate ester and replacement active are formed in the same reactor.

Replacemen/Modification of C8–C22 Standard, Unbranched, Substantially Saturated Monocarboxylic Acid In addition to (or in place of) partially replacing isethionate, it is also possible to replace the standard $C_8$ to $C_{22}$ straight chained, substantially saturated monocarboxylic acid normally used in the DEFI process.

The fatty acid replacement may be:

(1) any triglyceride derived from plant, animal or vegetable sources (for use in transesterification or transamidation process); or (2) any linear, straight, branched, or cyclic compound, saturated and/or partially unsaturated compound containing one or more free carboxylic acid moieties.

Examples of fatty acid replacements include compounds containing such carboxylic acid moiety derived from plant, animal or vegetable source (e.g., fatty acids derived from tallow fat, Neem and/or caster oil).

Also included are heteroatom containing compounds, such as ethoxylated fatty acids (e.g., Neodol® surfactants sold by Shell) and silicone based carboxylic acids and the like, such as those described by Imperatore (U.S. Pat. No. 5,300,666) sold/manufactured by Dow corning and Siltech Inc. and prepared by the reaction of any polymer with a terminal silanic hydrogen with a terminal vinyl containing carboxy compound and polycarboxylic acids, (such as dicarboxylic acids including adipic acid, azeleic acid, suberic acid, sebacic acid, 1, 12 dodecanedicarboxylic acid, 1, 14 tetradecanedicarboxylic acid, C21 dicarboxylic acid such as described in U.S. Pat. No. 4, 476,055, and the like).

Other compounds which may be fatty acid replacements are substituted acids and/or anhydrides, such as those prepared via the condensation of alpha-olefins with maleic acid and succinic acid (these are produced by Shell as described in JAOCS 71(7) 695–703 (1994) in "A Novel dianionic surfactant from the reaction of C14 alkenyl succinic anhydride with sodium isethionate"); and alpha-sulfo fatty acids such as those described by Hung in J. Ind. Chem. 15(3) 317–21 (1987). Both references are incorporated by reference into the subject application.

Among the multiple carboxylic acid replacements which can be used are dicarboxylic such as adipic acid, and 1, 12 dodecanedicarboxylic acid.

Compositions of the invention will have foam values as measured by defined protocol of about 40 and higher, preferably about 50 milliliters mls and higher, more preferably 50 to about 230. It should be understood that foaming values are to some extent dependent on the size of vessel used to generate foam but that, in general, good foam values were always seen.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight.

EXAMPLES

Protocol

Foaming Measurement Protocol (Examples 1–25)

One gram of final active mix is placed in a 100 mL glass stoppered graduated cylinder and dispersed in 20 mL of distilled de-ionized water; it is heated to 45° C. in a water bath until the temperature of the dispersion is at equilibrium. The sealed cylinder is then shaken vigorously for 60 seconds after which time the foam volume is measured in mL and recorded.

Protocol for Examples 26–36

One gram of final active mix is placed in a 250 mL glass-stoppered graduated cylinder and dispersed in 20 mL of distilled, de-ionized water; it is heated to 45° C. in a water bath until the temperature of the dispersion is at equilibrium. (note: For measurements done at 20° C., the water bath is set to 20° C. and the same procedure is followed). The sealed cylinder is then shaken vigorously for 60 seconds after which time the foam volume is measured in mL and recorded.

Mildness (Zein Solubilization)

The intrinsic mildness/irritation potential of these surfactant mixtures was evaluated using the standard Zein assay as described in Gotte et al., Chem. Phys. Appl. Surface Active Subst.; Proc. Int. Cong. $4^{th}$ (1964), vol. 3, pp 83–90, hereby incorporated by reference into the subject application.

This test is based on the correlation noted between the amount of zein solubilized by an aqueous surfactant solution and its irritancy; the more zein a surfactant dissolves, the greater its intrinsic irritation potential. The procedure is conducted gravimetrically: a 1% aqueous solution of surfactant mixture is added to 1.5 g of zein protein and this mixture is allowed to stir at a constant rate for one hour. This mixture is then centrifuged (for approximately 25 minutes at 4000 rpm) and the undissolved zein is isolated, rinsed and allowed to dry in a vacuum over at 60° C. to constant weight. The zein solubilized is determined by difference.

Process

The preparation of the surfactant mixtures studied for this invention used standard direct esterification conditions (1.35:1 molar ratio of fatty acid to isethionate, ZnO catalyst at 0.1118% of the total weight of reactants, heated at 238° C. for 90 minutes) except that part of the sodium isethionate reactant or fatty acid reactant was removed and replaced with an equimolar amount of co-reactant or co-reactant mix. Lauric acid was used as the fatty acid unless otherwise specified. In addition, the stearic acid addition and fatty acid stripping after reaction completion was omitted in the bench reactions noted in Tables 1, 2 and 3 (see Examples). It should be noted that partial reactant replacements can be added at the beginning of the reaction or they can be added at later stages depending on the extent of co-surfactant formation desired. Co-reagents can be added and reacted during the stripping step as well.

The following is a specific example for the modification using a replacement of 1/7 (14.29% by weight) of the sodium isethionate with pentaerythritol.

A glass reactor consisting of a 100 ml cylindrical bottom piece and a 4-neck glass top piece which is fitted with a thermocouple, a mechanical stirrer, a nitrogen gas inlet tube and distillation apparatus was charged with 9.38 g of sodium isethionate (0.06206 mol), 1.44 g of pentaerythritol (0.01037 mol), 20.02 g of lauric acid (0.09794 mol), and 0.347 g of ZnO. The vessel was heated using a heating mantle connected to a temperature controlled heating unit. At ~45° C., the fatty acid began to melt and the nitrogen sparging was initiated; when the temperature stabilized at 103° C. the water distilled off along with a small portion of the fatty acid (and some pentaerythritol). Once all the water was removed, the reaction was heated to 235–238° C. for 90 minutes. The reaction was allowed to cool to room temperature where it solidified to a white solid. The solid was crushed into a powder using a mortar and pestle.

Comparative Plus Examples 1–11

In addition to a control, where no isethionate was replaced, applicants prepared examples 1–11 where anywhere from 1/8 to 1/2 of the isethionate (on a weight basis) were replaced by a single compound (e.g., glycerol) or mixture of compounds (e.g., glycol and citric acid at defined ratio).

Table 1 below shows what and how much was replaced, color of solid made, zein results and foam values.

TABLE 1

| Example | Quantity (wt.) NaI replaced/coreactant | Color | % Zein Solubilized | Foam Vol (mL) |
|---|---|---|---|---|
|  | SLI - Control | White | 49 | 89.5 |
| 1 | ½/glycerol | White | 0 | 1 |
| 2 | ¼/glycerol | White | 0 | 42.6 |
| 3 | ⅛/glycerol | White | 33 | 60.5/71.5 |
| 4 | ¼/citric acid* | Pale yellow | 9 | 68/65 |
| 5 | ¼/citric acid | Pale yellow | 11 | 44/54 |
| 6 | ¼/glycerol:citric acid (1:1) | Very pale beige | 25 | 62.5 |
| 7 | ½/glycerol:lactic acid (1:1) | White | 26 | 44 |
| 8 | ⅓/glycerol:lactic acid (1:1) | White | 26 | 43/62 |
| 9 | ¼/glycerol:lactic acid (1:1) | White | 38 | 56/61.5 |
| 10 | ¼/glycerol:lactic acid (1:2) | White | 37 | 45.5 |
| 11 | ¼/glycerol:lactic acid (2:1) | White | 25 | 67/58 |

*Using a 1:1 fatty acid:co-reactant stoichiometry

As seen from Table 1, in almost all cases, % zein solubilized was significantly reduced (correlated with greater mildness) relative to control.

The foam volumes did not rise to the level of the control (89.5 mL) but did provide adequate foaming (e.g., defined as anything having foam of about 40 ml and higher, preferably 50 ml and higher).

EXAMPLES 12–20

TABLE 2

| Example | Quantity (Wt.) NaI or FA replaced/coreactant | % Zein Solubilized | Foam Vol. (mL) |
|---|---|---|---|
| SLI DEFI (Control) |  | 60 | 95 |
| 12 | Water | 11.3 | 0 |
| 13 | ¼/glycerol | 24 | 65 |
| 14 | ¼/gly:lac (2:1) | 25 | 61 |
| 15 | ¼/1, 12 DDC* | 40 | 90 |
| 16 | ¼/azeleic | 5 | 71 |
| 17 | ¹⁄₁₀/pentaerythritol | 32 | 82 |
| 18 | ⅛/taurine | 43 | 84 |
| 19 | ⅛/pentaerythritol | 30 | 87 |
| 20 | ½/pentaerythritol | 21 | 95 |

*Fatty acid replacement rather than isethionate
1, 12 DDC = 1, 12 dodecane dicarboxylic acid As seen from Table 2 above, either isethionate or fatty acid (Example 15) may be partially replaced. Further, again, in relation to SLI (zein % of 60), replacement of one reactant or other significantly reduced zein every time. Moreover, in the case of pentaerythritol, values of foam were very near or equal to those for reaction where there was no replacement. Foam values were again adequate, particularly for pentaerythritol.

EXAMPLES 21–25

To further test effect of the pentaerythritol, pentaerythritol was used to partially replace anywhere from $\frac{1}{10}$ to $\frac{1}{4}$ of isethionate as shown in Table 3 below:

TABLE 3

| Example | % Isethionate Replaced by Pentaerythritol | Foaming (mL) | Zein Solubilized |
|---|---|---|---|
| 21 | ¹⁄₁₀ | 78/85* | 33 |
| 22 | ⅛ | 90/84* | 30 |
| 23 | ⅐ | 95 | 15/27* |
| 24 | ³⁄₁₆ | 58 | 7.67 |
| 25 | ¼ | 6/11* | ** |

*2 runs
**No zein was solubilized in this example. While not wishing to be bound by theory this may be because of residual surfactant entrained in the zein may be picking up water.

As noted, zein was significantly reduced in all cases and, except where too much pentaerythritol was added (e.g., about 25%), foaming remained quite high.

COMPARATIVE AND EXAMPLES 26–31

Another example of partial isethionate replacement is the replacement of, on a weight basis, $\frac{1}{12}$ of starting isethionate with n-methyl taurine.

More particularly Isethionate (10.07 g) was mixed in a bench scale DEFI reactor with coconut fatty acid (20.5 g) and n-methyl taurine (0.996 g) and ZnO catalyst. Half of the normal amount of sodium isethionate used in a standard DEFI reaction was replaced with n-methyl taurine. The compounds were reacted at 238° C. for 90 minutes. Table 4 below (Examples 26–31) shows an analysis of the product formed for several such reactions:

TABLE 4

| Ingredient | Example 26 | Example 27 | Example 28 | Example 29 | Example 30 | Example 31* |
|---|---|---|---|---|---|---|
| DEFI | 52.500 | 66.500 | 68.000 | 64.300 | 70.400 | 63.200 |
| Iseth | 12.350 | 11.990 | 15.620 | 13.730 | 9.650 | 9.090 |
| Coconut Fatty Acid | 31.700 | 17.200 | 10.300 | 18.300 | 15.000 | 22.950 |
| Free Amine (n-methyl taurine) | 0.809 | 1.000 | 1.130 | 0.700 | 1.400 | 1.060 |
| Amide Product | 2.570 | 3.320 | 4.780 | 2.990 | 3.480 | 3.620 |

In Table 5 below, we see performance of the modified DEFI mixtures versus a DEFI control.

TABLE 5

| Modified DEFI Reaction | Foam at 45° C. | Foam at 20° C. | Zein |
|---|---|---|---|
| DEFI* | 135/153 | 86/79.5/63.5 | 51.67%/57% |
| Example 26 | 176/180 | 146/83/94.5 | 36.7% |
| Example 27 | 130 | 126/113.5/100 | 54.67%/56.7% |
| Example 28 | 201 | 131/151 | 52.3% |
| Example 29 | 166 | 90/106 | 56.7% |
| Example 30 | 165 | 108/109.5 | 50.3% |
| Example 31 (scale-up) | 208 | 77 | 38.3% |
| Coco N-Methyl Taurate (Comparative) | 135 | 122 | 50.0% |

*DEFI compound was the standard material coming from the DEFI reactor.

From bench examples (Example 26–30) and scale-up (Example 31) it appears the scale up reaction (Example 31) provides a performance benefit at 45° C.

It can be seen that foam activity of examples is generally superior to that of standard DEFI at 45° C. Further at 20° C., real performance benefit is seen. Specifically, foam value of examples are consistently higher than foam values of DEFI at 20° C. in almost all examples.

Zein data shows that the replacement molecules maintain foam boost without sacrificing mildness. The scale-up example was used primarily to show that reaction can be made using equipment similar to that used in current plant production.

Coco N-methyl taurate example shows that mixture examples of invention give foam boost relative to a non-mixture such as coco N-methyl taurate.

What is claimed is:

1. A final composition product comprising a mixture of:
   (a) an alkali metal, straight chain, saturated $C_8$ to $C_{22}$ ester of isethionate produced by the reaction of about 20% to 50% by wt. Alkali metal isethionate and about 35% to 75% by wt. Straight chain saturated $C_8$ to $C_{22}$ monocarboxylic fatty acid; and
   (b) a compound produced by the reaction of:
      (i) $C_8$ to $C_{22}$ straight chain, saturated monocarboxylic acids; and
      (ii) a compound which replaces a portion of the alkali metal isethionate used to make the ester of (a) and which is selected from the group consisting of pentaerythritol, taurine, N-methyltaurine and mixtures thereof;
      wherein (a) and (b) are produced in the same reactor under the same conditions; and
      wherein the amount of compound (ii) replacing said alkali isethionate of (a) is 5% to 75% of the isethionate, on a weight basis.

2. A final composition product according to claim 1, wherein said (ii) compound is pentaerythritol.

3. A final composition product according to claim 1, wherein said (II) compound is taurine or N-methyltaurine.

4. A method of making a final composition product comprising a mixture of claim 1, wherein said method comprising:
   (1) mixing reactants comprising about 20% to 50% by wt. alkali metal isethionate, about 35% to 75% by wt. straight chain saturated $C_8$ to $C_{22}$ monocarboxylic fatty acid and a compound selected from the group consisting of pentaerythritol, taurine, N-methyltaurine and mixtures thereof; wherein the amount of compound (ii) replacing said alkali isethionate of (a) is 5% to 75% of the isethionate, on a weight basis; and
   (2) reacting said reactants in the same reactor under the same conditions to form said final composition product.

5. A method of making a final composition product according to claim 4, wherein said (ii) compound is pentaerythritol.

6. A method of making a final composition product according to claim 4, wherein said (ii) compound is taurine or N-methyltaurine.

* * * * *